United States Patent [19]

Berger et al.

[11] Patent Number: 5,688,830
[45] Date of Patent: Nov. 18, 1997

[54] TREATMENT OF NEUROPATHIC PAIN

[75] Inventors: Jacob Berger, Los Altos Hills; Lee Allen Flippin, Woodside; John Cureton Hunter, Saratoga; David Garrett Loughhead, Belmont; Robert James Weikert, Woodside, all of Calif.

[73] Assignee: Syntex (U.S.A.) Inc., Palo Alto, Calif.

[21] Appl. No.: 782,700

[22] Filed: Jan. 16, 1997

Related U.S. Application Data

[60] Provisional application No. 60/011,048 Jan. 25, 1996.
[51] Int. Cl.[6] .................. A61K 31/135; C07C 217/18
[52] U.S. Cl. ............................................ 514/651; 564/353
[58] Field of Search ........................ 564/353; 514/651

[56] References Cited

U.S. PATENT DOCUMENTS

| | | | |
|---|---|---|---|
| 2,441,498 | 5/1948 | Löfgren et al. | 564/194 |
| 2,895,995 | 7/1959 | Willey et al. | 564/287 |
| 3,221,054 | 11/1965 | Arnold et al. | 564/353 |
| 3,475,455 | 10/1969 | Thoma et al. | 549/437 |
| 3,515,741 | 6/1970 | Thoma et al. | 558/422 |
| 3,659,019 | 4/1972 | Köppe et al. | 514/651 |
| 3,954,872 | 5/1976 | Köppe et al. | 564/353 |
| 4,031,244 | 6/1977 | Köppe et al. | 514/651 |
| 4,105,796 | 8/1978 | Köppe et al. | 514/651 |

FOREIGN PATENT DOCUMENTS

| | | |
|---|---|---|
| 691209 | 5/1967 | Belgium . |
| 1112839 | 5/1968 | United Kingdom . |

OTHER PUBLICATIONS

Lin et al., *Yaoxue Xuebao* (1984), vol. 19, No. 9, pp. 656–659, "Synthesis of Mexiletine Analogues".

Lin et al., *Acta Pharmaceutica Sinica* (1990), vol. 25, No. 2, pp. 150–153, "Synthesis and Antihypertensive Activity of Some Phenoxyalkylamine Compounds".

*Primary Examiner*—Richard L. Raymond
*Attorney, Agent, or Firm*—Brian Lewis; Janet K. Kaku

[57] ABSTRACT

This invention relates to a compound of the Formula I:

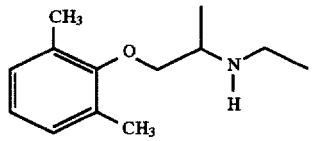

as a racemic mixture and its individual enantiomers, in particular the (R)-enantiomer, and their pharmaceutically acceptable salts. These compounds are useful as sodium channel blockers, and are particularly useful for the alleviation of neuropathic pain.

7 Claims, No Drawings

TREATMENT OF NEUROPATHIC PAIN

CROSS-REFERENCE TO RELATED APPLICATIONS

This application claims benefit under 35 U.S.C. 119(e) of U.S. Provisional Application No. 60/011,048, filed Jan. 25, 1996, now abandoned.

BACKGROUND OF THE INVENTION

1. Field of the Invention

This invention relates to a compound of the Formula I:

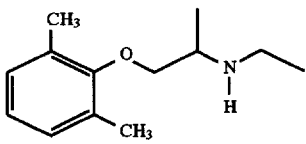

namely [2-(2,6-dimethylphenoxy)-1-methylethyl]-ethylamine and pharmaceutically acceptable salts thereof, to racemic and non-racemic mixtures thereof, and in particular to its (R)- enantiomer. The compound of Formula I is a sodium channel blocker, and thus exhibits useful pharmacological properties, in particular utility for the alleviation of neuropathic pain. The invention is also directed to formulations and methods for treatment.

2. Description of the Field

Neuropathic pain can be described as pain associated with damage or permanent alteration of the peripheral or central nervous system. Clinical manifestations of neuropathic pain include a sensation of burning or electric shock, feelings of bodily distortion, allodynia and hyperpathia.

Sodium channel-blocking agents have been reported to be effective in the treatment of various disease states. They are in particular useful as local anesthetics, and in the treatment of cardiac arrhythmia. It has also been reported for many years that sodium channel-blocking agents may be useful in the treatment of pain, including neuropathic pain; see, for example, Tanelian et al., *Pain Forum.*, 4(2), 75–80, (1995). There is evidence that sodium channel-blocking agents selectively suppress ectopic neural firing in injured nerves, and it is via this mechanism that they are believed to be useful for relieving pain. Studies carried out on well known sodium channel-blocking agents, for example carbamazepine, phenytoin, lidocaine, mexiletine, and the like have shown them to be useful against various types of neuropathic pain conditions (Swerdlow, 1984; McQuay et al.). However, pain relief has often been obtained concomitantly with numerous adverse events and/or limitations in efficacy which have restricted tolerability of these drugs.

Numerous sodium channel-blocking agents have been disclosed in the patent and non-patent literature. For example, mexiletine 2-(2,6-dimethylphenoxy)-1-methylethylamine, a well-known sodium channel-blocking agent and antiarrhythmic, is disclosed in U.S. Pat. Nos. 3,659,019, 3,954,872, and 4,031,244 (Köppe et al.).

Two Chinese references, *Yaoxue Xuebao*, 19(9), 656–659 (1984) and *Acta Pharmaceutica Sinica*, 25(2), 150–153 (1990), disclose mexiletine derivatives and analogues, their physical properties, and physiological activities. In particular, the references include mexiletine derivatives which have aromatic substitution in the amino position. They are said to have high α-adrenoceptor affinity and to be useful as antihypertensives. An abstract of the latter reference (CA 114:42158) depicts as an example of a compound included within the scope of this disclosure the structure 2-(2,6-dimethylphenoxy)-1-methylethyl]-propylamine. However, an English translation of this article does not appear to disclose such a derivative.

U.S. Pat. No. 2,441,498 (Löfgren et al.) discloses lidocaine, 2-(diethylamino)-N-(2,6-dimethylphenyl) acetamide, and its use as a local anesthetic and antiarrhythmic. U.S. Pat. Nos. 3,221,054 (Arnold et al.) discloses 1-(2,6-dimethylphenoxy)-2-methylaminopropane (alternatively named as [2-(2,6-dimethylphenoxy)-1-methylethyl]-methylamine) as useful as an intermediate in the synthesis of monoamine oxidase inhibitors, and 4,105,796 (Köppe et al.) discloses the same compound as useful for suppressing convulsions or alleviating cardiac arrhythmia. U.S. Pat. No. 2,895,995 (Willey et al.) discloses the preparation of local anesthetics β-(2,6-xylyloxyethyl)-dimethylamine and β-(2,6-xylyloxyethyl)-diethylamine and their quaternary ammonium salts. However, the use of lidocaine is limited by its potential for cardiotoxic and CNS side effects.

Published Great Britain Patent Application No. 1,112,839 discloses 1-(p-chloro)-2-ethylaminopropane, 1-(m-chloro)-2-ethylaminopropane, and 1-(2,3-dichloro)-2-ethylaminopropane compounds possessing anorexigenic activity, their preparation, and compositions. U.S. Pat. Nos. 3,475,455 and 3,515,741 (both to Thoma et al.) disclose 1-(3',4'-methylenedioxy-phenoxy)-2-aminopropane and 1-(cyanophenoxy-2-ethylamino)propane derivatives, respectively, their salts, preparation, and anorexigenic compositions. Published Belgium Patent Application No. 691, 209 discloses racemic or optically active 1-(4'-nitrilo)-phenoxy-2-ethylaminopropane and 1-(3',4'-methylenedioxy)-phenoxy-2-ethylaminopropane, their preparation and compositions.

The disclosures of these and other documents referred to throughout this application are incorporated herein by reference.

It can therefore be seen that a need still exists for an orally active agent that is effective for the treatment of neuropathic pain, but having low side effects. We have discovered a compound which surprisingly displays this desired spectrum of activity, namely [2-(2,6-dimethylphenoxy)-1-methylethyl]-ethylamine, and in particular its (R)-enantiomer.

The compound of Formula I is unexpectedly more active in standard assays when compared with close analogues, for example, [2-(2,6-dimethylphenoxy)-1-methylethyl]-methylamine and [2-(2,6-dimethylphenoxy)-1-methylethyl]-propylamine and isomers thereof.

In addition, for drugs that are racemic mixtures it is well known that the therapeutic activity usually resides in one of the enantiomers. The other enantiomer may be pharmacologically inactive, or have different therapeutic activities. Surprisingly, the (R)- and the (S)-enantiomers of [2-(2,6-dimethylphenoxy)-1-methylethyl]-ethylamine both display similar activity in neuropathic pain models, but deleterious side effects are largely confined to the (S)-enantiomer.

SUMMARY OF THE INVENTION

A first aspect of the present invention relates to a compound of Formula I:

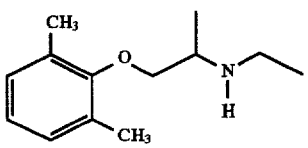

and in particular to the individual (R)- enantiomer, i.e., (R)-[2-(2,6-dimethylphenoxy)-1-methylethyl]-ethylamine, and pharmaceutically acceptable salts thereof.

A second aspect of this invention relates to pharmaceutical compositions containing the compound of Formula I, in admixture with one or more suitable excipients.

A third aspect of this invention relates to use of the compound of Formula I for treating neuropathic pain conditions in a mammal that is responsive to sodium channel-blocking agents, including:

peripheral neuropathies, such as trigeminal neuralgia, postherpetic neuralgia, diabetic neuropathy, glossopharyngeal neuralgia, lumbar and cerical radiculopathy, and neuropathy secondary to metastatic infiltration, adiposis dolorosa, and burn pain; and central pain conditions following stroke, thalamic lesions and multiple sclerosis, by administering a therapeutically effective amount of a compound of Formula I to the mammal.

DETAILED DESCRIPTION OF THE INVENTION

Definitions:

As used herein:

It should be understood that Formula I as drawn is intended to represent the racemic form of Formula I as well as the individual enantiomers and non-racemic mixtures thereof. The racemic form is named as [2-(2,6-dimethylphenoxy)-1-methylethyl]-ethylamine, and the two enantiomers are (R)-[2-(2,6-dimethylphenoxy)-1-methylethyl]-ethylamine and (S)-[2-(2,6-dimethylphenoxy)-1-methylethyl]-ethylamine. The individual enantiomers may be obtained by resolving a racemic or non-racemic mixture of an intermediate at some appropriate stage of the synthesis, or by resolution of a compound of Formula I. It is understood that the individual enantiomers as well as racemic and non-racemic mixtures of enantiomers are encompassed within the scope of the present invention. When the compound of Formula I is a pure enantiomer, the stereochemistry is specified by either R or S according to the Cahn-Ingold-Prelog R—S system. In this manner relative stereochemistry is conveyed unambiguously.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

"Mammal" includes humans and all domestic and wild mammals, including without limitation, cattle, horses, swine, sheep, goats, dogs, cats, rabbits and the like.

"Pharmaceutically acceptable" refers to that which is useful in preparing a pharmaceutically composition that is generally safe, non-toxic, and neither biologically nor otherwise undesirable, and includes that which is acceptable for veterinary use as well as human pharmaceutical use.

"Pharmaceutically acceptable salts" refers to those salts which are pharmaceutically acceptable, as defined above, and which possess and retain the desired pharmacological activity of the compound of Formula I. The compound of Formula I form acid addition salts by virtue of the presence of the basic nitrogen atom. Acid addition salts may be formed with inorganic salts such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, p-toluenesulfonic acid, camphorsulfonic acid, 4-methylbicyclo[2.2.2.]oct-2-ene-1-carboxylic acid, glucoheptonic acid, 4,4'-methylenebis(3-hydroxy-2-ene-1-carboxylic acid, 3-phenylpropionic acid, trimethylacetic acid, tertiary butylacetic acid, lauryl sulfuric acid, gluconic acid, glutamic acid, hydroxynaphthoic acid, salicyclic acid, stearic acid, muconic acid, tartaric acid and the like. Preferred pharmaceutically acceptable salts of [2-(2,6-dimethylphenoxy)-1-methylethyl]-ethylamine are acid addition salts formed from inorganic acids. A particularly preferred pharmaceutically acceptable salt is [2-(2,6-dimethylphenoxy)-1-methylethyl]-ethylamine hydrochloride.

"Treatment" as used herein covers any treatment of a condition in a mammal, particularly a human, and includes:

(i) preventing the disease from occurring in a subject which may be predisposed to the disease, but has not yet been diagnosed as having it;

(ii) inhibiting the condition, i.e., arresting its development; or (iii) relieving the condition, i.e., causing regression of the disease.

The term "disease state which is alleviated by treatment with a sodium channel blocker" as used herein is intended to cover all disease states which are generally acknowledged in the art to be usefully treated with sodium channel blockers in general, and those disease states which have been found to be usefully treated by the specific sodium channel blocker of our invention, the compound of Formula I. Such disease states include, but are not limited to, cardiac arrhythmia, pain associated with damage or permanent alteration of the peripheral or central nervous system, for example peripheral neuropathies, such as trigeminal neuralgia, postherpetic neuralgia, diabetic neuropathy, glossopharyngeal neuralgia, and neuropathy secondary to metastatic infiltration, adiposis dolorosa, and burn pain; and central pain conditions following stroke, thalamic lesions and multiple sclerosis.

The term "therapeutically effective amount" refers to that amount which is sufficient to effect treatment, as defined above, when administered to a mammal in need of such treatment. The therapeutically effective amount will vary depending on the subject and disease state being treated, the severity of the affliction and the manner of administration, and may be determined routinely by one of ordinary skill in the art.

"Analgesia" is an absence of pain in response to a stimulus that would normally be painful.

"Allodynia" refers to a condition in which a normally innocuous sensation, such as pressure or light touch, is perceived as being extremely painful.

"$E_{max}$" refers to the maximal effect of a drug in a particular assay.

"$ED_{50}$" identifies the dose of a drug that elicits 50% of the maximal drug effect.

2-(2,6-Dimethylphenoxy)-1-methyl-ethylamine, also known as mexiletine, is identified herein as a compound of Formula II:

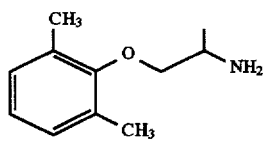

[2-(2,6-Dimethylphenoxy)-1-methylethyl]-methylamine is identified herein as a compound of Formula III:

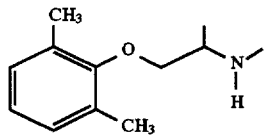

[2-(2,6-Dimethylphenoxy)-1-methylethyl]-propylamine is identified herein as a compound of Formula IV:

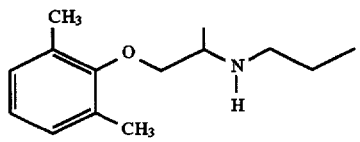

UTILITY

The compound of Formula I and its pharmaceutically acceptable acid addition salts thereof have been found to possess valuable pharmacological properties. In particular, they have been shown to be useful as sodium channel blockers in standard laboratory tests. Accordingly this compound and pharmaceutically acceptable compositions containing them are useful in the regulation of physiological phenomena related to sodium channel blockade, including cardiac arrhythmia, various epilepsies, pain associated with damage or permanent alteration of the peripheral or central nervous system, for example peripheral neuropathies, such as trigeminal neuralgia, postherpetic neuralgia, diabetic neuropathy, lumbar and cervical radiculopathy, glossopharyngeal neuralgia, and neuropathy secondary to metastatic infiltration, adiposis dolorosa, and burn pain; and central pain conditions following stroke, thalamic lesions and multiple sclerosis.

TESTING

Interaction with ligand binding sites on voltage-gated sodium channels is determined in radioligand binding assays, described in Example 10.

Potential for sodium channel blocking activity is determined in vitro by the method of Kourtney and Stricharz (1987), Local Anasthetics, Springer-Verlag, New York, described in Example 11.

The mechanical allodynia activity is determined in vivo, described in Example 12.

The cold allodynia activity is determined in vivo, described in Example 13.

METHODS OF PREPARATION

Preparation of Compound of Formula I

The racemic compound of Formula I is prepared from the intermediate of Formula (1), as shown below in Reaction Scheme I.

REACTION SCHEME I

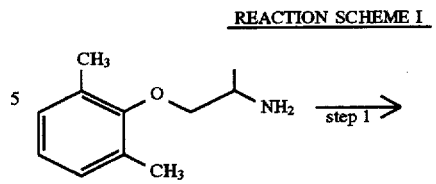

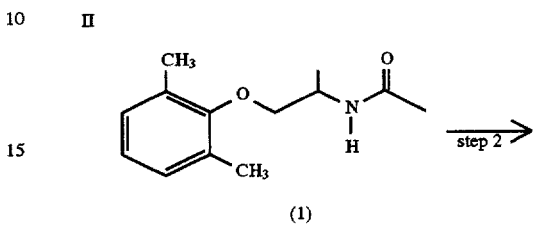

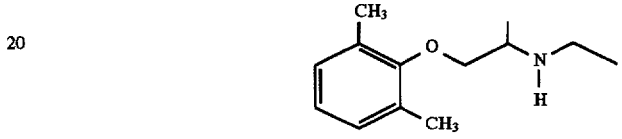

Preparation of a Compound of Formula I

Step 1—Preparation of a Compound of Formula (1)

In Step 1, 2-(2,6-dimethylphenoxy)-1-methyl-ethylamine (mexiletine) is converted to mexiletine acetamide. Mexiletine is treated with an acetylating agent, such as an acetyl chloride or acetic anhydride, in the presence of concentrated aqueous alkali and an organic solvent, e.g., ethyl acetate. The reaction temperature is maintained at about 0°–25° C., preferably below 10° C., for about 10 minutes to 3 hours, preferably about 35 minutes. Following completion of the reaction, the resulting N-[2-(2,6-dimethylphenoxy)-1-methylethyl]-acetamide is isolated by conventional techniques, and used as such in Step 2.

It should be noted that replacing racemic mexiletine with one of its enantiomers and carrying out the above reactions gives N-[2-(2,6-dimethylphenoxy)-1-methylethyl]-acetamide in optically active form.

Step 2—Preparation of a Compound of Formula I

Step 2 involves the reduction of the N-[2-(2,6-dimethylphenoxy)-1-methylethyl]-acetamide to the amine. The product from step 1 is heated to reflux temperature in the presence of an aprotic solvent such as tetrahydrofuran, and an effective reducing agent such as borane-dimethylsulfide complex. The reaction temperature is maintained at reflux for about 5–40 hours, preferably about 24 hours, and is preferably performed under an inert atmosphere, e.g., nitrogen. When the reaction is substantially complete, the product is isolated and purified by conventional techniques, for example converting to an acid salt, preferably the hydrochloride salt, then crystallizing from an organic solvent, for example ethanol/ether, yielding racemic [2-(2,6-dimethylphenoxy)-1-methylethyl]-ethylamine salt, preferably the hydrochloride salt.

It should be noted that replacing the racemic compound of Formula (1) with N-[2-(2,6-dimethylphenoxy)-1-methylethyl]-acetamide in optically active form gives the compound of Formula I in optically active form.

Preparation of Analogues of the Compound of Formula I

Similarly, two analogues of the compound of Formula I compounds were prepared for comparison purposes, namely

[2-(2,6-dimethylphenoxy)-1-methylethyl]-methylamine and [2-(2,6-dimethylphenoxy)-1-methylethyl]-propylamine. The methylamine analogue is prepared by first reacting the compound of Formula II by methods well known in the art, for example with ethyl chloroformate, and then reducing the carbamate thus produced with lithium aluminum hydride. The propylamine analogue was prepared in the same manner as shown above for a compound of Formula I, replacing acetyl chloride by propionyl chloride.

Resolution of a Compound of Formula I

The compound of Formula I may be resolved into its enantiomers by conventional resolution means, for example, by separation (e.g., fractional crystallization) of the diastereomeric salts formed by the reaction of a compound of Formula I (as its free base) with an optically active acid, at temperatures between 0° C. and the reflux temperature of the solvent employed for fractional crystallization, for example isopropanol. Exemplary of such optically active acids are the optically active forms of camphor-10-sulfonic acid, 2-bromo-camphor-10-sulfonic acid, camphoric acid, menthoxyacetic acid, tartaric acid, malic acid, diacetyltartaric acid, pyrrolidine-5-carboxylic acid, and the like, preferably tartaric acid. The separated pure diastereomeric salts may then be cleaved by standard means, such as treatment with a base, to afford both enantiomers of the compound of Formula I.

For example, resolution with D-tartaric acid gives the (R)-enantiomer of the compound of Formula I; starting with L-tartaric acid gives the (S)-enantiomer.

Alternatively, the (R)- and (S)- enantiomers of the compound of Formula I are prepared as described above, i.e., acetylation of optically pure mexiletine, followed by reduction of the acetamide thus produced.

EXAMPLES

The invention is illustrated without limitation by the following Examples.

Example 1

Preparation of a Compound of Formula (1)

1A. Acetyl chloride (99 ml, 1.39 mol, 1.5 eq) was added to a stirred suspension of mexiletine hydrochloride (200 g, 0.927 mol), ethyl acetate (750 ml), and 5N sodium hydroxide (750 ml) over a period of 35 minutes while keeping the temperature at ≦10° C. After the addition was complete, the reaction was allowed to stir for 45 minutes at 15–20° C. The mixture was then added to water (1 l) and the ethyl acetate layer separated. The aqueous layer was washed with ethyl acetate (2×300 ml) and the combined ethyl acetate layers were washed with saturated aqueous sodium bicarbonate until the washings were no longer acidic. The ethyl acetate solution was then washed with brine, dried over MgSO$_4$, and concentrated to give N-[2-(2,6-dimethylphenoxy)-1-methylethyl]-acetamide (197 g, 96% yield, mp 85–85.8° C.).

1B. Similarly, replacing acetyl chloride with ethyl chloroformate, [2-(2,6-dimethylphenoxy)-1-methylethyl]-carbamic acid ethyl ester was made.

1C. Similarly, replacing acetyl chloride with propionyl chloride, [2-(2,6-dimethylphenoxy)-1-methylethyl]-propionamide was made.

Example 2

Preparation of a Compound of Formula I

2A. Borane-dimethylsulfide complex (10–10.2M, 35 ml, 1.2 eq) was added to a refluxing solution of N-[2-(2,6-dimethylphenoxy)-1-methylethyl]-acetamide (68 g, 0.289 mol) and tetrahydrofuran (400 ml) under a nitrogen atmosphere. After the addition was complete, the reaction was allowed to reflux for 25 hours. The reaction was then cooled to room temperature and 10% hydrochloric acid/ethanol was added until the mixture was acidic. After concentration of the reaction mixture, ethyl ether was added to induce crystallization. The solids were isolated by filtration and dried to give [2-(2,6-dimethylphenoxy)-1-methylethyl]-ethylamine hydrochloride salt (53.0 g, 75% yield, mp 184.7–185.8° C.).

2B. Similarly, replacing N-[2-(2,6-dimethylphenoxy)-1-methylethyl]-acetamide with [2-(2,6-dimethylphenoxy)-1-methylethyl]-carbamic acid ethyl ester, and replacing borane-dimethylsulfide complex with lithium aluminum hydride, [2-(2,6-dimethylphenoxy)-1-methylethyl]-methylamine was made.

2C. Similarly, replacing N-[2-(2,6-dimethylphenoxy)-1-methylethyl]-acetamide with [2-(2,6-dimethylphenoxy)-1-methylethyl]-propionamide, [2-(2,6-dimethylphenoxy)-1-methylethyl]-propylamine was made.

Example 3

Preparation of the Enantiomers of the Compound of Formula I

3A. An aqueous solution of racemic [2-(2,6-dimethylphenoxy)-1-methylethyl]-ethylamine hydrochloride (41.1 g, 0.169 mol) was made alkaline with potassium hydroxide and extracted with ethyl acetate (3×250 ml). The combined ethyl acetate layers were washed with brine, dried over MgSO$_4$, and concentrated to give the free base (36 g). The free base was dissolved in isopropanol (750 ml), and D-tartaric acid (25.3 g, 0.168 mol) was added. The resultant solid was filtered, dried, and recrystallized to give (1R, 2'S, 3'S)-(-)-[2-(2,6-dimethylphenoxy)-1-methylethyl]-ethylamine tartrate salt (18.5 g, mp 161.4–162.7° C., $[\alpha]_D$=−19.0°, 97% ee as determined by chiral HPLC analysis).

An aqueous solution of the tartrate salt (18.0 g) was made alkaline with aqueous potassium hydroxide and washed with ethyl acetate (4×250 ml). The combined ethyl acetate layers were washed with brine, dried over MgSO$_4$, and concentrated to give an oil. This oil was dissolved in ethyl ether (500 ml) and made acidic with anhydrous hydrochloric acid in ether. The precipitated solids were isolated by filtration and recrystallized from ethyl alcohol to give (R)-(-)-[2-(2,6-dimethylphenoxy)-1-methylethyl]-ethylamine hydrochloride salt (8.3 g, 75% yield, mp 187–187.4° C., $[\alpha]_D$=−11.8).

3B. Similarly, replacing D-tartaric acid with L-tartaric acid and following the procedure of 3A above, (S)-(+)-[2-(2,6-dimethylphenoxy)-1-methylethyl]-ethylamine hydrochloride was prepared.

Example 4

This example illustrates the preparation of a representative pharmaceutical formulation for oral administration containing an active compound of Formula I, e.g., (R)-(-)-[2-(2,6-dimethylphenoxy)-1-methylethyl]-ethylamine hydrochloride.

| Ingredients | Quantity per tablet, mgs. |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I can be used as the active compound in the preparation of the orally administrable formulations of this example.

Example 5

This example illustrates the preparation of another representative pharmaceutical formulation for oral administration containing an active compound of Formula I, e.g., (R)-(-)-[2-(2,6-dimethylphenoxy)-1-methylethyl]-ethylamine hydrochloride.

| Ingredients | Quantity per tablet, mgs. |
|---|---|
| Active Compound | 400 |
| Cornstarch | 50 |
| Lactose | 145 |
| Magnesium stearate | 5 |

The above ingredients are mixed intimately and pressed into single scored tablets.

Other compounds of Formula I can be used as the active compound in the preparation of the orally administrable formulations of this example.

Example 6

This example illustrates the preparation of a representative pharmaceutical formulation containing an active compound of Formula I, e.g., (R)-(-)-[2-(2,6-dimethylphenoxy)-1-methylethyl)]-ethylamine hydrochloride.

An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.1 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

Other compounds of Formula I can be used as the active compound in the preparation of the orally administrable formulations of this example.

Example 7

This example illustrates the preparation of a representative pharmaceutical formulation for oral administration containing an active compound of Formula I, e.g., (R)-(-)-[2-(2,6-dimethylphenoxy)-1-methylethyl]-ethylamine hydrochloride.

An injectable preparation buffered to a pH of 4 is prepared having the following composition:

| Ingredients | |
|---|---|
| Active Compound | 0.2 g |
| Sodium Acetate Buffer Solution (0.4 M) | 2.0 ml |
| HCL (1 N) | q.s. to pH 4 |
| Water (distilled, sterile) | q.s. to 20 ml |

Other compounds of Formula I can be used as the active compound in the preparation of the injectable formulations of this example.

Example 8

This example illustrates the preparation of a representative pharmaceutical formulation for topical application containing an active compound of Formula I, e.g., (R)-(-)-[2-(2,6-dimethylphenoxy)-1-methylethyl]-ethylamine hydrochloride.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I can be used as the active compound in the preparation of the topical formulations of this example.

Example 9

This example illustrates the preparation of a representative pharmaceutical formulation containing an active compound of Formula I, e.g., (R)-(-)-[2-(2,6-dimethylphenoxy)-1-methylethyl]-ethylamine hydrochloride.

A suppository totalling 2.5 grams is prepared having the following composition:

| Ingredients | |
|---|---|
| Active Compound | 500 mg |
| Witepsol H-15* | balance |

(*triglycerides of saturated vegetable fatty acid; a product of Riches-Nelson, Inc., New York, N.Y.)

Other compounds of Formula I can be used as the active compound in the preparation of the suppository formulations of this example.

Example 10

Radioligand Binding Assays

The following assays characterize the interaction of the compounds of Formula I with ligand binding sites on voltage-gated sodium channels.

10A. Preparation of cell membranes

Frozen tissues were obtained from Pel-Freez Biologicals (Rogers, AR). Tissues were homogenized in 10 volumes of a Tris-sucrose buffer (10 mM Tris-HCl, 250 mM sucrose, pH 7.4 at 4° C.) using 10 strokes with a glass-glass, hand-held homogenizer. The homogenates were filtered through nylon mesh and then centrifuged at 1,000×g for 15 minutes. The pellets were resuspended in a Hepes buffer (50 mM Hepes, 130 mM choline chloride, 5 mM glucose, 5.4 mM KCl, pH 7.4 at 4° C.). The resuspended pellets were centrifuged at 1,000×g for 15 minutes, resuspended in a Hepes buffer (50 mM Hepes, 130 mM choline chloride, 5 mM glucose, 5.4 mM KCl, pH 7.4 at 25° C.) and, frozen at −70° C. until used in binding assays.

10B. [$^3$H]BTX Binding Assay

Cell membranes prepared as in Example 10A above were incubated with 16 nM [$^3$H]BTX in 250 µl of Hepes buffer (50 mM Hepes, 130 mM choline chloride, 5 mM glucose, 5.4 mM KCl, pH 7.4 at 25° C.). Nonspecific binding was defined in the presence of 1 mM veratridine. Unless otherwise specified, PbTx (0.1 µM) and LqTx (50 µg/ml) were included in the assays. Membranes were incubated for 60 minutes at 25° C. and then filtered using GF/B glass fiber filters that had been pretreated with 0.3% PEI. Filters were rinsed with 3×1 ml of ice cold 50 mM Tris-HCl (pH 7.4 at 4° C.) and the bound radioactivity was determined by scintillation counting (Packard Top-count).

The racemate of Formula I inhibited [$^3$H]BTX binding in rat cortex, rat heart, and rat dorsal root ganglion tissue membranes. The potency of the racemate was found to be approximately 10 fold greater in the rat cortex than in rat heart or rat dorsal root ganglion. Similar potencies were obtained with mexiletine. There was no difference in the potencies of the (R)- or (S)-enantiomers of Formula I in inhibiting [$^3$H]BTX binding to rat brain cortex membranes. This indicates that the racemate and the (R)- and (S)-enantiomers are sodium channel ligands which inhibit channel function by binding to the local anesthetic site on the channel.

10C. [$^3$H]STX Binding Assay

Membranes as prepared in Example 10A above were incubated at 37° C. for 30 minutes in 250 µl of a Hepes buffer (50 mM Hepes, 130 mM choline chloride, 5.5 mM glucose, 0.8 mM MgSO$_4$, 5.4 mM KCl, pH 7.4 at 37° C.) containing 1 nM [$^3$H]STX. Nonspecific binding was defined with 1 µM tetrodotoxin (TTX). Reactions were terminated by filtration through GF/B glass fiber filters pretreated with 0.1% PEI. The filters were rinsed with 3×1 ml ice cold H$_2$O and the bound radioactivity determined in a Packard 1900 liquid scintillation counter using Aquasol scintillation fluid.

The racemate of Formula I exhibited no detectable affinity for the [$^3$H]STX binding site on the rat brain sodium channel.

10D. [$^3$H]PD85639 Binding Assay

Membranes as prepared in Example 10A above were incubated with 3 nM [$^3$H]PD 85639 in 250 µl of Hepes buffer (50 mM Hepes, 130 mM choline chloride, 5 mM glucose, 5.4 mM KCl, pH 7.4 at 25° C. with Tris base). Nonspecific binding was defined in the presence of 0.1 mM PD85639. Membranes were incubated for 60 minutes at 25° C. and then filtered using GF/B glass fiber filters that had been pretreated with 0.3 % PEI. Filters were rinsed with 3×1 ml of ice cold 50 mM Tris-HCl (pH 7.4 at 4° C.) and the bound radioactivity was determined by scintillation counting (Packard Top-count).

The racemate of Formula I inhibited [$^3$H]PD85639 to the local anesthetic site of the sodium channel in rat brain cortex membranes. Mexiletine exhibited similar affinity estimates.

10E. [$^{14}$C]Guanidinium Ion Influx Binding Assay

Chinese hamster ovary cells stably expressing the rat brain type IIA sodium channel subunit were maintained in RPMI 1640 with 10% fetal bovine serum and 300 µl/ml G-418. Chinese hamster lung cells stably expressing the human heart (hH1a) sodium channel subunit were maintained in DMEM with 5% fetal bovine serum and 300 µg/ml G-418. Both cells were subcultured and grown to confluence in 24-well plates 2–3 days before each experiment. After the growth medium was removed, the cells were washed with warm buffer (25 mM Hepes-Tris, 135 mM choline chloride, 5.4 mM potassium chloride, 0.98 mM magnesium sulfate, 5.5 mM glucose, and 1 mg/ml BSA, pH 7.4) and incubated in buffer on a 36° C. slide warmer for approximately 10 minutes. Various concentrations of the test compounds or standard sodium channel blockers (10 µl) and then veratridine (100 µM) were added to each well. After the cells were exposed to veratridine for 5 minutes, 5 µM of [$^{14}$C] guanidinium was added, incubated with the radioligand, washed with 4 ml of ice-cold buffer, and dissolved in 0.1N sodium hydroxide. The radioactivity and the protein concentration of each cell lysate were determined by liquid scintillation counting and the protein assay using Pierce BCA reagent.

The racemate of Formula I inhibited veratridine-stimulated [$^{14}$C]Guanidinium ion influx through both rat brain and human heart sodium channels with the similar potencies being exhibited through rat brain and human heart sodium channels.

Example 11

Test for Blockade of Sodium Channels—in Vitro Assay

This assay demonstrates the ability of the compounds of Formula I to function as sodium channel blockers, by producing a blockade of high frequency nerve activity in the rat vagus nerve.

Vagus nerves were removed from rats, continually superfusing them with control solutions or solutions of the compounds under test. Electric shocks were applied to the nerve to stimulate the propagation of nerve impulses. The amplitude of the synchronous compound action potential was measured; it was reduced as the sodium channels became blocked by the perfused compounds.

There is good agreement between the sodium channel blocking potency as determined by this assay and those measured by other methods, for example the voltage-clamping technique. The compounds of our invention showed activity as sodium channel blockers in this test.

Example 12

Mechanical Allodynia In Vivo Assay

This assay determines the effectiveness of compounds in relieving one of the symptoms of neuropathic pain produced by spinal nerve ligation, namely mechanical allodynia.

12A. The Surgery

The surgical procedure was performed essentially as described by Kim and Chung, *Pain*, (1992) 50:355–363. Briefly, the rats were anesthetized with an intraperitoneal dose of pentobarbital sodium (65 mg/kg) with additional doses of anesthetic given as needed. Each animal was then placed in a prone position, a 3 cm lateral incision was made, and the left paraspinal muscles separated from the spinous process at the L$_4$-S$_2$ level. The L$_6$ transverse process was then removed in order to visually identify the L$_4$-L$_6$ spinal nerves. The L$_5$ and L$_6$ spinal nerves were then individually

13 isolated and tightly ligated with silk thread. The wound was then closed in layers by silk sutures.

12B. The Mechanical Allodynia Assay

Seven to 28 days post-surgery, a calibrated series of eight von Frey filaments were used to assess mechanical allodynia. Animals were housed individually in plexiglass cages with a wire mesh floor. Filaments of increasing stiffness were applied perpendicular to the midplantar surface in the sciatic nerve distribution areas of the left hindpaw and were slowly depressed (4–6 seconds) until bending occurred. The filament application order and number of trials were determined by the up-down method of Dixon (Chaplan, et al., *J. Neurosci. Methods*, (1994) 53:55–63). Flinching and licking of the paw and paw withdrawal on the ligated side were all considered positive responses. The 50% paw withdrawal threshold (g) was then calculated and compared to control.

12C. The Selection of Doses

The doses for the acute and chronic studies were selected on the basis of prior assessment of the acute effects on the test compounds on the gross behavior in normal rats. Briefly, the rats were weighed and grouped into cages, dosed with the test compound, and observed continuously for changes in behavior. At 60 and 120 minutes post-dose, the rats were observed for pinna, corneal and righting reflexes. Pinna and corneal reflexes were tested by using a piece of natural hair from a brush that is attached to a glass rod. The righting reflexes were tested by placing the rat flat on its back, and recording the time it takes for the animal to right itself onto all four legs. The posture and gait were assessed by placing the rat on the floor.

12D. The Results of Subcutaneous Administration

| Compound Formula | Chiral form | Dose (mg/kg) | $ED_{50}$ | $ED_{max}$ |
|---|---|---|---|---|
| I | racemate | 3–60 | 12.6 | 66% |
| II | racemate | 30–100 | no value at these doses | 29% |
| III | racemate | 10–100 | 31.3 | 67% |
| IV | racemate | 10–30 | not tested due to adverse events at higher doses | |

The results show that after subcutaneous administration, the compound of Formula I was considerably more potent ($ED_{50}$) than II or III in the mechanical allodynia test. Compound IV was less potent than compound III ($ED_{50}$ >30 mg/kg) and further escalation of the dose-range was prevented by the onset of adverse events, including convulsions and severe ataxia at 60 mg/kg.

In contrast, when tested in this assay the (R)-enantiomer of Formula I exhibited significantly greater maximal analgesic activity (98% $E_{max}$) in vivo against mechanical allodynia than either the racemate of I (66% $E_{max}$), the racemate of II (29% $E_{max}$), and the racemate of III (67% $E_{max}$).

12E. The Results of Oral Administration

The results show that after oral administration, the (R)- or (S)-enantiomers of Formula I or the racemate of Formula II did not produce analgesia against mechanical allodynia. However, the (S)-enantiomer of I was associated with adverse side effects at doses greater than 60 mg/kg, whereas the (R)-enantiomer of I exhibited a cleaner safety profile with overt adverse effects occurring only at doses ≧300 mg/kg.

14

Example 13

Cold Allodynia In Vivo Assay

This assay determines the effectiveness of compounds in relieving one of the symptoms of neuropathic pain produced by unilateral mononeuropathy, namely cold allodynia.

13A. The Surgery

Unilateral mononeuropathy was produced in rats using the Chronic Constriction Injury model performed essentially as described by Bennet and Xie, *Pain*, (1988) 33:87–107. Briefly, the rats were anesthetized with an intraperitoneal dose of pentobarbital sodium (65 mg/kg) with additional doses of anesthetic given as needed. The lateral aspect of each rat's hind limb was shaved and scrubbed with Novasan. Using aseptic technique, an incision was made on the lateral aspect of the hind limb at the mid-thigh level. The biceps femoris was bluntly dissected to expose the sciatic nerve. On the right hind limb of each rat, four loosely tied ligatures were made around the sciatic nerve approximately 1–2 millimeters apart. On the left side of each rat, an identical dissection was performed except that the sciatic nerve was not ligated. The muscle was closed with a continuous suture pattern, and the skin was closed with wound clips.

13B. The Cold Allodynia Assay

Each rat was placed individually into a plexiglass chamber with a metal plate 6 cm from the bottom. This chamber was filled with ice water to a depth of 2.5 cm above the metal plate, with the temperature of the bath maintained at 0° C. throughout the experiment. A timer was started, and the rat's response latency was measured to the nearest tenth of a second. A "response" was defined as a rapid withdrawal of the right ligated hindpaw completely out of the water while the animal was stationary and not pivoting. An exaggerated limp while the animal was walking was not scored as a response. Maximum immersion time was 20 seconds with a 20 minute interval between trials. The screening criteria were 1) the average of two trials was less than or equal to 13 seconds, and 2) there was consistency across the two trial scores. Animals were screened for hypersensitivity to cold on post-surgery days 4 through 10, and selected for inclusion in dose-response studies based on the criteria described above. The pre-dose screening values were used as the animal's baseline cold allodynia scores.

13C. The Experimental Design

For acute studies, the animals received either subcutaneous or oral injections and were tested for cold allodynia at 1, 3, and sometimes 5 hours post-dose.

For chronic studies, the animals received subcutaneous or oral injections twice daily for 4 days and once on day 5. The animals were tested for allodynia on day 1 at 1, 3 and 5 hours following the 8 am dose, and at 5 hours following the 8 am dose on days 3 and 5. Two days later, the animals were tested for cold allodynia to assess whether there was a wash-out of the drug being tested. Following this screening for cold allodynia, the animals in two of the three chronic studies received either subcutaneous or oral injections of the drug at a dose previously shown to produce significant antiallodynic effects acutely. One hour after this dosing, the animals were again tested for cold allodynia.

13D. The Selection of Doses

The selection of doses was similar to that of Example 12C.

13E. The Results of Subcutaneous Administration— Acute Studies

| Compound | Chiral Form | Dose mg/kg | ED₅₀ 1 hr | ED₅₀ 3 hr | Eₘₐₓ 1 hr | Eₘₐₓ 3 hr |
|---|---|---|---|---|---|---|
| I | racemate | 10–60 | 15.7 | N/D | 82% | N/D |
| I | (S)- | 10–60 | 12.8 | 10.0 | 100% | 58% |
| I | (R)- | 10–100 | 37.0 | 23.4 | 91% | 87% |
| II | racemate | 10–100 | 29.8 | 33.6 | 73% | 80% |
| III | (R)- | 10–100 | 26.1 | 31.4 | 76% | 74% |
| IV | (R)- | 10–60 | 28.4 | 29.9 | 74% | 74% |

N/D = not able to determine.

Example 13E shows the results for the acute studies following subcutaneous administration. The compounds of Formula I, III and IV when tested as the (R)-isomer exhibited comparable potency (ED$_{50}$), but compound I as the (R)-isomer exhibited significantly greater maximal analgesic activity (E$_{max}$) than III or IV in the inhibition of cold allodynia. It should be noted that the racemate and the (S)-enantiomer of Formula I were associated with adverse side effects, including convulsions and immobility, at doses higher than 60 mg/kg; the (R)-enantiomer of Formula IV produced behavioral problems, including splayed limbs and abnormal righting reflexes, at doses higher than 60 mg/kg. The (R)-enantiomer of Formula I, on the other hand, exhibited a greater maximal analgesic activity, a cleaner safety profile with adverse side effects not observed until doses of 300 mg/kg were used, and a longer duration of action in vivo over the racemate, (S)-enantiomer, or II.

13F. The Results of Subcutaneous Administration—Chronic Studies

For the chronic studies administered subcutaneously, the doses of compound I that were inactive in the acute studies (5 mg/kg for the racemate produced no significant anti-allodynic effects when tested at 1, 3 or 5 hours post-dose; however, after 5 days of twice daily dosing, the racemate and (R)-isomer produced significant levels of anti-allodynia.

13G. The Results of Oral Administration—Chronic Studies

Chronic studies administered orally on compounds of Formula I and II were also conducted. The results showed that chronic sub-threshold doses (10 and 20 mg/kg for the (R)-enantiomer) can produce as robust an anti-allodynic effect as an acute dose of compound I that is 10 fold higher.

In contrast, the compound of Formula II demonstrated no anti-allodynic effect when tested chronically.

13H. The Discussion of Results

It has been shown that the compound of Formula I when administered orally to a mammal is metabolized to some extent to the compound of Formula II. The levels of compound of Formula II found in the plasma after oral administration of the (R)-enantiomer of Formula I was 5–10 fold less than that found after the acute administration of compound of Formula II itself. This study clearly demonstrates that the anti-allodynic effects of the compound of Formula I do not arise as a result of the presence of compound of Formula II due to metabolization, but are a consequence of the anti-allodynic action of compound I.

What is claimed is:

1. A compound of the formula:

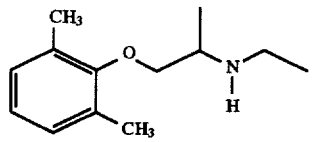

namely [2-(2,6-dimethylphenoxy)-1-methylethyl]-ethylamine, or a pharmaceutically acceptable salt thereof.

2. The (R)-enantiomer of a compound of claim 1, namely (R)-[2-(2,6-dimethylphenoxy)-1-methylethyl]-ethylamine, or a pharmaceutically acceptable salt thereof.

3. The compound of claim 2, wherein the pharmaceutically acceptable salt is (R)-[2-(2,6-dimethylphenoxy)-1-methylethyl]-ethylamine hydrochloride.

4. The compound of claim 2, wherein the pharmaceutically acceptable salt is (R)-[2-(2,6-dimethylphenoxy)-1-methylethyl]-ethylamine tartrate.

5. A pharmaceutical composition comprising a therapeutically effective amount of a compound of claim 1, or a pharmaceutically acceptable salt thereof, in admixture with at least one pharmaceutically acceptable non-toxic carriers.

6. A method for treating a mammal having a disease state which is alleviable by treatment with a sodium channel blocker, comprising administering to a mammal in need thereof a therapeutically effective amount of a compound of claim 1, or a pharmaceutically acceptable salt thereof.

7. The method of claim 6, wherein the disease state is neuropathic pain.

* * * * *